United States Patent [19]

Makoui et al.

[11] Patent Number: 5,104,411
[45] Date of Patent: Apr. 14, 1992

[54] FREEZE DRIED, CROSS-LINKED MICROFIBRILLATED CELLULOSE

[75] Inventors: Kambiz B. Makoui, Menasha, Wis.; Pronoy K. Chatterjee, Spotswood, N.J.

[73] Assignee: McNeil-PPC, Inc., Milltown, N.J.

[21] Appl. No.: 938,373

[22] Filed: Dec. 9, 1986

Related U.S. Application Data

[63] Continuation of Ser. No. 757,567, Jul. 22, 1985, abandoned.

[51] Int. Cl.$^5$ ................ D06M 13/12; A61F 13/15; A61F 13/20; C08B 00/00
[52] U.S. Cl. ................ 8/116.4; 8/116.1; 162/157.1; 536/56; 604/375; 604/904; 604/358
[58] Field of Search ........... 8/116.1, 116.4; 241/28, 241/DIG. 37; 536/56; 106/122, 163.1; 527/305, 306; 162/146, 157 C

[56] References Cited

U.S. PATENT DOCUMENTS

| 3,241,553 | 3/1966 | Steiger | 128/156 |
| 3,658,613 | 4/1972 | Steiger | 241/28 |
| 3,932,209 | 1/1976 | Chatterjee | 162/157.6 |
| 4,474,949 | 10/1984 | Chatterjee et al. | 536/56 |

Primary Examiner—Prince Willis, Jr.
Assistant Examiner—John F. McNally

[57] ABSTRACT

Absorbent retentive pulp is described which is capable of retaining good absorbency even after having been highly compressed. The pulp is produced by mixing a microfibrillated pulp slurry with a cross-linking agent followed by freeze drying.

29 Claims, No Drawings

FREEZE DRIED, CROSS-LINKED MICROFIBRILLATED CELLULOSE

This is a continuation of application Ser. No. 757,567, filed July 22, 1985 now abandoned.

BACKGROUND OF THE INVENTION

This invention relates to absorbent, retentive cellulose pulp which is capable of retaining good absorbency even after having been highly compressed. This pulp is provided for use in absorbent products such as sanitary napkins, catamenial tampons, diapers, dressings or the like which are used for absorbing body fluids.

For many years, cellulose pulp has been utilized for absorbing body fluids. Wood pulp has been found most suitable for such products primarily because it is an inexpensive, readily available absorbent material. Such wood pulp is generally derived from soft wood trees such as southern pine and the like and is commercially treated in chemical pulping processes such as the kraft or sulfite processes during which the trunks and branches of trees are reduced to wood pulp fibers and non-fibrous substances such as gums, resins and lignin are chemically removed. The resulting wood pulp is sometimes bleached and then formed into board for subsequent disassociation into pulp fluff to be used in the aforementioned products.

Although pulp fluff derived from the conventional process steps has, in the past, been successfully employed in body fluid absorption products, the art has increasingly sought to improve the absorption capacity and fluid retention properties of wood pulp. Many suggestions have already been advanced, generally directed towards chemical modifications of the cellulose polymer of which the wood pulp fibers are composed. While these efforts have met with some success, the resulting products are substantially more expensive than native wood pulp and suffer from some peculiar drawbacks such as brittleness or slow wicking rates. It has long been known that the absorbency of cellulosic fibers may be improved by wet cross-linking the fibers. Thus, U.S. Pat. No. 3,241,553 discloses such cross-linking in order to provide absorbent fibrous products which have improved absorbency as well as the ability to retain greater amounts of absorbed fluids when subjected to pressures which tend to squeeze out the fluids absorbed. There is, however, no disclosure in said U.S. Pat. No. 3,241,553 concerning the cross-linking of microfibrillated fibers.

The need for a relatively inexpensive, simple process for treating native cellulose fibers to increase their absorption capacity and fluid retention properties has been met to a limited degree by the process disclosed by Chatterjee, et al. in U.S. Pat. No. 4,474,949. Chatterjee, et al. disclosed a process of mechanically beating a dispersion of cellulose fibers to a degree such that at least the outermost of the secondary walls of the cellulose fibers were essentially completely disintegrated to microfibrillar form followed by the freeze drying of the beaten dispersion. The resultant material possesses excellent absorption properties at low densities, but poor absorption properties at higher densities. In addition, the mechanical strength of this material is too low since it collapses in contact with water under a confining pressure.

Accordingly, there is a need for a relatively inexpensive, simple process for treating native cellulose fibers to increase their absorption capacity and fluid retention properties, not only at low densities but also at higher densities.

SUMMARY OF THE INVENTION

In accordance with the objects and principals of the present invention, a highly absorbent, retentive, cellulose fiber is provided, which fiber retains good absorbency and retention even after having been highly compressed.

The absorbent retentive pulp of the invention is produced by forming a dilute slurry, in a freeze drying medium, of cellulose fibers which have been beaten to a degree such that at least the outermost secondary walls thereof are essentially completely disintegrated into microfibrillar form. The freeze drying medium consists either of water or a non-aqueous solvent, such as t-butyl alcohol, which is capable of hydrogen bonding with cellulose and which in pure form, possesses a freezing point between 0° C. and 100° C. or a boiling point between 0° C. and 150° C. at normal pressure. A cross-linking agent is then added to the slurry and cross-linking is permitted to commence. The dispersion is then dried by the process of freeze drying, whereby the water or solvent is first frozen by the application of refrigeration means and then the resulting ice or frozen solvent is removed by sublimation, i.e., the ice or solid frozen solvent is converted into the gaseous state without first passing into the liquid state and the gas is carried away leaving a substantially water or solvent free product. Sublimation is accomplished generally by subjecting the frozen dispersion to a low pressure environment. Preferably, the pulp is pressed in order to produce a densified thin sheet.

The structure of the cellulose pulp derived from the teachings of this invention is similar to that disclosed in U.S. Pat. No. 4,474,949 which is incorporated herein by reference. Thus, as can be seen from the micrographs in U.S. Pat. No. 4,474,949, the fibrils released from the starting cellulose fibers by the beating step appear, after the dispersion is cross-linked and freeze dried, to be in the form of discrete platelets or sheets comprising said freed fibrils in compressed form. The sheets tend to appear as discontinuous walls surrounding and defining cellular voids. Macroscopically, it is believed that this morphology results in the sponge-like appearance of the freeze dried pulp. Although the microscopic structure of the product of the present invention is similar to that of the product of U.S. Pat. No. 4,474,949, nevertheless the cross-linking step of the present process provides a pulp which has a surprisingly increased absorption capacity and fluid retention even after having been highly compressed, the cross-linking having formed intermolecular cross-links between macromolecular chains. Such compressed product is also highly resilient (demonstrating a Z direction swelling) in the wet state. The expression "Z direction" as used herein is intended signify the direction of initial compression of the compressed product.

DETAILED DESCRIPTION OF THE INVENTION

In accordance with the invention, there is provided a dilute dispersion (preferably in aqueous medium) of fibrous cellulose which has been beaten to an extensive degree to free microfibrils from the fibrous structure. Water is the preferred medium in which this initial beating takes place. However, other suitable non-aqueous media may also be utilized for this purpose.

While the preferred form of the starting cellulose fibers is chemical wood pulp derived from such pulping processes as kraft or sulfite pulping, it will be understood that almost any source of cellulose fibers is suitably employed. Accordingly, in addition to wood pulp, such diverse sources of cellulose fibers may include hemp, baggase, cotton and the like.

Irrespective of the plant source, cellulose fibers comprise cellulose chains, consisting of cellobiose units, laid down in a parallel arrangement with the long chained molecules strongly associated through secondary forces e.g. hydrogen bonds. This association of the cellulose chains results in a very uniform crystalline structure known as micelles or microcrystallites. The micelles are associated in the plant into long thread-like structures known as microfibrils. The association of the micelles into microfibrils is such that spaces or dislocations exist between micelles; such spaces, being of the order of about 15-20 angstrom units (Å), allowing liquid to migrate into the microfibril and accounting for at least part of the absorbency and retention properties of the cellulose fiber. High magnification photographs show that microfibrils of wood cellulose are filaments about 35 Å in breadth with a periodic variation in electron density along their lengths. Based on this observation, it has been proposed that the wood pulp microfibril is in the shape of a flat ribbon wound in the form of a tight helix.

The cellulose fiber itself is composed of layers of associated microfibrils. The outer layer is termed the primary wall and the inner layers are termed secondary walls which are further classified as $S_1$, $S_2$ layers, etc.

As described above, it is known, in the art of making paper, to beat or mechanically work a fiber slurry to free some microfibrils on the very outer layer of the cellulose fiber. The purpose of this beating treatment in the paper art is to enhance bonding. Great care, heretofore, has been taken to avoid damaging the inner layers.

In accordance with the teachings of U.S. Pat. No. 4,474,949, such a beating step is carried further to the point where at least the outermost of the secondary walls is essentially completely disintegrated to microfibrillar form. Preferably, the starting cellulose fibers are first dispersed in a dilute aqueous slurry. Such a slurry should have a solid content ranging from about 0.5 to about 10.0% and still more preferably, from about 1.5 to about 6.0%.

The slurry is next passed to a beating station where it is mechanically worked to free microfibrils to a suitable degree. The method and apparatus for beating the slurry are not critical provided that a sufficient degree of microfibrillation is accomplished. Accordingly, commercially available equipment such as the Hollander, Jordan, or disk refiner type of beaters may be employed. The Hollander beater is an apparatus wherein the slurry is introduced into a tub and forced to pass under the nip formed between a corregated roller and a plate. As the roller is turned, a shearing force is exerted on the fibers in the nip. The Jordan type of beater employs two nesting cones with an annular space in between. The inner cone reciprocates so that the slurry, introduced into the annular space, is sheared. In the disk refiner, two round plates are in a face to face relationship and at least one of the plates is provided with ribs and at least one of the plates rotates. The slurry is introduced between the faces of the plates and is sheared by the rotating action.

There exists still other suggestions for producing microfibrillar pulp and these are equally useful in carrying out this invention. One such suggestion is found in U.S. Pat. No. 4,374,702 issued on Feb. 22, 1983 to Turbak, et al.

It has been found that sufficient bearing has occurred when the resulting fibers have been reduced to a Canadian Standard Freeness value of less than 100 and preferably less than 50. The period of time during which a slurry of a particular dilution, with a particular type of fiber is beaten in a particular beating apparatus is easily correlated to the Canadian Standard Freeness value of the finished product by a series of simple experiments. It will be understood that because the parameters which effect beating time may vary greatly and still produce a beaten slurry usable in accordance with the teachings of this invention, no generalization can be made with respect to such beating time.

In said U.S. Pat. No. 4,474,949, when using a Valley Beater, Model No. 73-13-1-1/2 Niagra, obtained from the Voith Company of Appleton, Wis. and beating a slurry of loblolly pine bleached kraft pulp having a solid content of 2%, suitable beating times ranged from 120 to about 160 minutes.

The microfibrillated pulp, utilized in accordance with the present invention may be prepared by soaking a southern pine bleached kraft pulp board with water and beating it on a Valley Beater at a consistency of 2%. The percentages of ingredients in the slurry are given herein as weight of the ingredient in grams for each 100 ml of slurry. A cross-linking agent is then added to the resultant slurry of microfibrillated fibers and cross-linking is permitted to commence. Thereafter the slurry is freeze dried, whereby a highly absorbent, retentive, cross-linked cellulose pulp results. It should be noted that if it is desired to utilize a non-aqueous freeze drying medium, such as t-butyl alcohol, in the instance wherein the initial beating of the fibers was carried out in an aqueous medium the water in the slurry of microfibrillated fibers is first exchanged with the non-aqueous t-butyl alcohol medium before the cross-linking agent is added. The t-butyl alcohol is used in order to save energy since it freezes at 25° C., and need not be frozen to 0° C. as is the case with water.

In accordance with the cross-linking procedure, such as that taught in U.S. Pat. No. 3,241,553, cellulosic fibers are subjected to a chemical treatment whereby they are chemically modified to form bonds between the hydroxyl groups in the cellulose molecules. The reactive groups of the cross-linking agent which combines with the hydroxyl groups may exist prior to the reaction with cellulose, as in the case of glyoxal, or they may be generated during the reaction with the cellulose, as in the case of the sodium thiosulfate derivative of divinylsulfone. In order to cross-link cellulose, the cross-linking agent must be at least difunctional with respect to cellulose, e.g., it must react with at least two hydroxyl groups. Formaldehyde, for example, is monofunctional with regard to many substances; it is, however, difunctional with respect to cellulose and is therefore a suitable cross-linking agent. Cellulose may be dry cross-linked or wet cross-linked. However, the procedure utilized in accordance with the present invention is wet cross-linking.

A common technique known in the art is to apply the cross-linking agent and a catalyst to the cellulose in an aqueous bath, driving off the water in a drying step, and reacting the cross-linking agent with the cellulose in a subsequent heat curing step. The expression "heat curing" as used herein is intended to signify cross-linking by application of heat. Wet cross-linked cellulose is obtained when the cross-linking agent is reacted with the cellulose while the cellulose fibers are not collapsed but are in a swollen state. Ordinarily, the cellulose fibers are maintained in a swollen state by water which is present during the reaction. However, techniques have been developed whereby the cellulose fibers can be maintained in a swollen state in the absence of water by using in lieu thereof an inert, non-volatile substance. Cellulose fibers so treated have the properties of wet cross-linked cellulose even though the reaction takes place in the absence of significant amounts of water. Suitable agents for the cross-linking of cellulose are formaldehyde, difunctional aldehydes such as glutaraldehyde; dichloro acetic acid, dichloro propanol-2, diepoxides, such as butadiene diepoxide and polyepoxides such as the compound marketed by Shell Chemical Company under the name Eponite 100, N-methylol acrylamide, and divinylsulfone. Most of the above materials require alkaline catalysts, such as sodium hydroxide, to produce wet cross-linked cellulose. However, for the purposes of the present invention, the preferred cross-linking agent is glutaraldehyde, the preferred catalyst utilized in conjunction therewith being zinc chloride. Glutaraldehyde is used in many medical devices and is thus safe (as for instance the device disclosed in U.S. Pat. No. 4,274,410). Zinc chloride was chosen because it not only permits the cross-linking or/polymerization to occur, but it also causes swelling of cellulose which imparts higher resilient characteristics to the final product.

Additional wet cross-linking agents include: condensation products of formaldehyde with organic compounds, such as urea or other chemical compounds which contain at least two active hydrogen groups, particularly dimethylolurea, dimethylol ethyleneurea and imidazolidine derivatives; dicarboxylic acids; dialdehydes such as glyoxal; diisocyanates; divinyl compounds; dihalogen-containing compounds such as dichloracetone and 1,3-dichloropropanol-2; halohydrins such as epichlorohydrin etc.

In the instance wherein the freeze drying medium is a non-aqueous solvent such as t-butyl alcohol, the preferred cross-linking agent is a commercially available polyamine/amide-epichlorohydrin adduct which is manufactured by Hercules under the tradename Polycup 2002. No catalyst is needed in conjunction with the latter cross-linking agent.

The fibers are in a swollen state at the time of cross-linking in order to obtain wet cross-linked cellulose. Although this swelling is normally achieved by cross-linking in the presence of water, other swelling agents may be used, such as the preferred zinc chloride referred to above.

Cellulose molecules consist of a large number of glucose units linked to each other through glucoside linkages (oxygen bridges). The preferred catalyst, zinc chloride, reacts with glucoside linkages to form an oxonium salt. This reactive product is more polar and enables the non-reactive cellulose to swell to a greater degree.

One of the preferred cross-linking agents of the present invention, namely glutaraldehyde, undergoes a condensation reaction with cellulose with the loss of water to form an intermolecular cross-link between macromolecular chains. The reaction of cellulose with glutaraldehyde takes place through the formation of hemiacetal and acetal linkages. The addition of glutaraldehyde in the presence of zinc chloride, to the beaten pulp slurry with the subsequent removal of water causes the formation of polyglutaraldehyde and cross-linking of cellulosic fibers. Good results have also been obtained, in accordance with the present invention when 37% W/V of formalin was used in place of glutaraldehyde as the cross-linking agent. The expression "% W/V of formalin" as used herein is intended to designate weight of formalin in grams for every 100 ml of aqueous solution.

In the instance wherein t-butyl alcohol is to be used as the freeze drying medium, dewatered microfibrillated cellulose is mixed with t-butyl alcohol at 2% consistency and 12.5% to 25% of Polycup 2002 (based on the weight of the fiber) is added to the slurry as the cross-linking agent. This precedes the freeze drying step which is the next step in the process of the present invention.

Other freeze drying media suitable for use in the present invention are as follows:

|  | Melting Point °C. | Boiling Point °C. |
|---|---|---|
| benzene | 5.5 | 80.1 |
| hexafluorobenzene | 5.3 | 80.5 |
| 2-nitroisobutane | 26 | 127 |
| acetic acid | 16.6 | 118 |
| t-butyl mercaptan | 1.1 | 64.2 |
| cyclohexane | 6.5 | 80.7 |
| cyclohexyl fluoride | 13 | 100.2 |
| ethylene dibromide | 9.8 | 131 |
| 1,2-difluoro tetrachloroethane | 25 | 93 |
| glyoxal | 15 | 50.4 |
| 2,2 dimethyl propionitrile | 16 | 105 |

After the reaction with the cross-linking agent, the slurry is then subjected to freeze drying, irrespective of whether the freeze drying medium is water or a non-aqueous polar solvent such as t-butyl alcohol. By freeze drying, it is meant that the slurry is subjected to refrigeration means sufficient to solidify the water or non-aqueous polar solvent therein. The frozen slurry is then subjected to conditions wherein the ice or solid non-aqueous solvent sublimates directly into the gaseous state without first passing through the liquid state and the gaseous water or solvent is removed.

Various means may be utilized for effecting the freezing step such as passing the slurry into an externally refrigerated compartment and retaining the slurry therein until frozen. Alternatively the slurry may be circulated around the source of refrigeration such as cooling tubes or a bath containing coolant, e.g., liquid nitrogen, dry ice, alcohol solution or the like and the frozen slurry collected.

To effect the sublimation and removal of water or non-aqueous solvent in the vapor phase, the frozen slurry is subjected to a subatmospheric pressure environment under which conditions water or solvent sublimates directly from the solid phase to the vapor phase.

Vacuum means for providing such a subatmospheric pressure environment are well known in the art of freeze drying. Typically such subatmospheric pressure is less than about 5.0 Torr and preferably less than about 0.5 Torr.

The resulting product is a sponge-like dried pulp which, either in the sponge-like state or when ground into pulp fluff, exhibits a substantial increase in liquid absorption and retention properties as contrasted with pulp provided by conventional means. The improvement in the absorption properties is probably a result of the unusal morphology resulting from preparing pulp by the teachings herein.

After the freeze dried product is washed and dried, if there should have been any impurities present, the dried products are pressed under high pressure in order to form a thin flat sheet. The resultant pressed product is capable of retaining good absorbency and retention and thus differs substantially from the product of U.S. Pat. No. 4,474,949 which does not include the cross-linking step. The product of the present invention compressed to a density of 0.4 g/cc, has a Porous Plate Capacity of at least 10 g/g with a testing fluid of 1% NaCl aqueous solution. Said compressed product has a Porous Plate Retention of at least 5 g/g with a testing fluid of 1% NaCl aqueous solution. Comparative data regarding cross-linked cellulose pulp and the product of U.S. Pat. No. 4,474,949 are given in Table 1.

The invention will be further described by reference to the following examples wherein there is disclosed preferred embodiments of the present invention. However, it is to be appreciated that such examples are illustrative but not limitative of the broader aspects of the inventive concept.

The percentages of ingredients in the slurry are given herein as weight of the ingredient in grams for each 100 ml of slurry.

EXAMPLE 1

The raw material was prepared by soaking a southern pine bleached kraft pulp board with water and beating it on a Valley Beater at a consistency of 2%. The Valley Beater, Model No. 73-13-1-1/2 Niagra, obtained from the Voith Company of Appleton, Wis., consists of an oval, open cast-iron tub, beater bars and bed plate. The stock is moved counterclockwise by rotation of the beater bars (500±10 rpm). The beating action takes place between bars and the bed plate. In order to prepare the raw material, initially, about 430 grams of air-dried pulp board (6.5% moisture) were soaked in 10 liters of water for a minimum of 4 hours. The pulp boards were then cut into small pieces and processed in the Valley Beater with an additional 10 liters of water for 10 minutes (no beating) to prepare a slurry of 2% consistency. The beating process, started by applying a load to the beater bars, was continued for a period of 4 hours. The beaten slurry was then placed in a reaction vessel and heated to 80° C. The reaction vessel is a unit manufactured by Dover Corporation. The unit (Model No. TA-40-SP-1972) is constructed of stainless steel and it is steamed jacketed for heating at maximum water pressure of 25 psi at 300° F. The maximum capacity of this unit is 100 liters. Mixing was carried out by a wall scraper. An appropriate amount of zinc chloride and glutaraldehyde was added for each 100 ml of slurry to obtain the following composition:

| Ingredient | gms/100 ml of Slurry |
|---|---|
| pulp | 2.0 |
| Zn Cl$_2$ | 1.6 |
| glutaraldehyde | 0.5 |

The mixture was stirred for one hour and then the reacted slurry was cooled to room temperature. The reacted slurry was then poured into a container and frozen to −25° C. for 24 to 72 hours as required. The freezing time was dependent on sample thickness. The freezer used was an upright frost-free freezer (Model No. 16-0F16K) manufactured by Amana. The maximum low temperature capability of the unit is −25° C. The frozen cake was then lyophilized in a cryolizer freeze dryer (Model No. B-64), manufactured by Brunswick Scientific Co. Inc. This unit has a vacuum drum on the top which contains three shelves which can be heated to a maximum temperature of 34° C. Frozen samples were placed in the freeze dryer and then subjected to vacuum. Volatile components were sublimed and drawn off by a vacuum pump. The vacuum pump was protected by a cold trap where most of the water vapor was condensed and frozen. The samples were sublimed in the freeze dryer at 34° C. for 48 hours. At the end of the drying period the samples were removed and washed. This washing consisted of soaking the freeze dried products and washing three times in tap water to remove excess chemicals. The samples were then dried in a forced hot-air oven for a period of two hours. Thereafter, the dried products were pressed to 1000 psi for a period of 10 seconds at 100° C. to a density of 0.4 g/cm$^3$. The press which was utilized is manufactured by Wabash Metal Products Company. It has a controlled heating system and possesses a 6-inch compression stroke and maximum compression force of 30 tons. The upper and lower plenums have the capability of heating to 300° C. The densified samples were then cut and stored in plastic bags for evaluation.

EXAMPLE 1A

The procedure of Example 1 was repeated utilizing formalin as the cross-linking agent rather than glutaraldehyde. Thus after the mixing step with the wall scraper, an appropriate amount of zinc chloride and formalin was added for each 100 ml of slurry to obtain the following composition:

| Ingredient | gms/100 ml of slurry |
|---|---|
| pulp | 2.0 |
| Zncl$_2$ | 1.0 |
| formalin | 0.7 |

The remainder of the procedure was the same as that of Example 1.

EXAMPLE 2 t-Butyl Alcohol Process

In this process, t-butyl alcohol (TBA), manufactured by ARCO Chemical Company and sold under the tradename of TEBOL 99, was used as the freeze drying medium. Pure t-butyl alcohol is a compound which freezes at 25° C. and has a boiling point of 82° C. High moisture level present in t-butyl alcohol will lower the freezing temperature of this compound. Therefore, high consistency beaten microfibrillated cellulose was washed four times with alcohol to remove the excess water. The dewatered microfibrillated cellulose was then mixed with t-butyl alcohol at 2% consistency and from 12.5% to 25% of Polycup 2002 (based on the weight of the fiber) placed in a petri dish and placed in a freezer for 30 minutes. Polycup 2002 is a polyamine/amide epichlorohydrin adduct which is a cross-linking agent manufactured by Hercules. No catalyst was used in conjunction with this cross-linking agent. The frozen cake was then placed in the freeze dryer described in Example 1 for 6 hours. Thereafter the semi-dry samples were placed in an oven at 100° C. for 1 hour. The dry sample was then pressed in the heated Wabash Metal Products Company press described in Example 1, to 1000 psi for a period of 10 seconds at 100° C. The density of the resulting sample was 0.4 g/cc.

For the purposes of the following discussion, the product of Example 1 is designated as MFCS-IIa meaning microfibrillated cellulose sheet-2a. The product of U.S. Pat. No. 4,474,949 prepared by microfibrillation with a beating time of 160 minutes and freeze drying, but without cross-linking, is designated as MFCS-I.

For testing the products of Examples 1 and 2, the following tests were carried out:

1. Wicking Test: This test determined the wicking characteristics of pulp board or hand sheets. The time to reach fluid to 10 cm mark on 1.5×13 cm strip was recorded.
2. The 7cc Absorption Test: 7cc of 1% aqueous NaCl were poured into an elliptical template which rested upon a test specimen. The time from the initial contact of liquid with the sample to the end of the absorption process was measured. Each sample tested measured 5×22.5 centimeters.
3. Fast Dynamic Form Test (Napkin Capacity): The napkin was attached to the sample holder and fluid was fed through an orifice to the napkin at the rate of 3.4 cc/min. The total amount of fluid absorbed by the product before fluid leaked through the cover was recorded as the total capacity of the napkins. Further details concerning this test are set forth in column 9 of U.S. Pat. No. 3,858,585.
4. The products of Examples 1 and 2 were tested for absorption properties at different densities by the porous plate method (Table 1).

The Porous Plate Testing apparatus, is described in detail in Textile Res. J. 37 pp. 356–366, 1967 and a modified testing procedure has been further described as "Gravimetric Absorbency Testing System" in a monograph on "Absorbency" in Textile Science and Technology, volume 7, page 67, edited by Pronoy K. Chatterjee, published in 1985 by Elsevier Science Publishers BV, P.O. Box 211, 1000 AE Amsterdam, The Netherlands. Briefly, this test involves placing the sample in what is essentially a Buchner Funnel having a porous bottom plate and holding the sample in place by applying thereon a standard weight to maintain a standardized confining pressure. The porous plate is placed in contact with a reservoir of fluid and the sample is allowed to absorb the fluid through the porous plate until saturated. By maintaining the samples at essentially the level of the reservoir, the fluid absorbed is subjected to essentially zero hydraulic head with respect to the reservoir. The weight of fluid absorbed, divided by the weight of the sample, is termed the Maximum Capacity. As the sample absorbs fluid, a measurement of weight absorbed as a function of time is made. The slope of this curve at the time absorption begins is termed the Initial Rate of Absorption. To determine fluid retention, the saturated sample is elevated with respect to the reservoir, thereby imposing a hydraulic head upon the fluid absorbed, the head being arbitrarily chosen as 35.5 cm. of fluid. The apparatus is provided with means for measuring the weight of fluid retained under the hydraulic head. Retention values are reported as the weight retained per unit weight of sample. The results of testing the samples are recorded below in Table 1. The testing fluid in each case is a 1% NaCl aqueous solution, and the confining pressure is 4.8 grams/cm$^2$.

TABLE 1

| Material | Beating Time (Min.) | Cross-Linking Treatment | Density g/cm$^3$ | Max Capacity g/g | Ret'n g/g | % Z Expn |
|---|---|---|---|---|---|---|
| Absorbency of Crosslinked Freeze-dried Microfibrillated Wood Pulp Cellulose Technique: Porous Plate wiothy 1% NaCl Solution | | | | | | |
| Wood Pulp Control (non-beaten) | 0 | None | 0.04 | 12 | 3 | 0 |
| freeze-dried | 0 | None | 0.40 | 5 | 4 | 0 |
| | 0 | glutaraldehyde + ZnCl$_2$ | 0.04 | 12 | 3 | |
| | 0 | glutaraldehyde + ZnCl$_2$ | 0.40 | 10 | 3 | 200 |
| Freeze dried Microfibrillated Cellulose Sheet | | | | | | |
| MFCS-I Product of U.S. Pat. No. 4,474,949 | 240 | None | 0.04 | 22 | 10 | 0 |
| | 240 | None | 0.40 | 6 | 5 | 0 |
| MFCS-IIa water: freeze drying medium) Example 1 | 240 | glutaraldehyde + ZnCl$_2$ | 0.04 | 20 | 10 | |
| | 240 | glutaraldehyde ZnCl$_2$ | 0.40 | 20 | 11 | 400 |
| MFCS-II Example 1A | 240 | 37% W/V of formalin + ZnCl$_2$ | 0.40 | 15 | 9 | |
| MFCS-IIb (Example 2) (t-butyl alcohol: freeze drying | 90 | Polycup 2002 | 0.40 | 14 | 6 | 300 |

TABLE 1-continued

Absorbency of Crosslinked Freeze-dried
Microfibrillated Wood Pulp Cellulose
Technique: Porous Plate wiothy 1% NaCl Solution

| Material | Beating Time (Min.) | Cross-Linking Treatment | Density g/cm$^3$ | Max Capacity g/g | Ret'n g/g | % Z Expn |
|---|---|---|---|---|---|---|
| medium) | | | | | | |

The conditions under which the pulp control were produced, were similar to the corresponding conditions for preparing the product of Example 1, except as noted in Table 1.

As can be seen from Table 1, the products of the present invention as set forth in Examples 1 and 2, are compared with freeze-dried non-beaten non-cross-linked (as well as cross-linked) wood pulp as well as the product of U.S. Pat. No. 4,474,949 (designated MFCS-1) which consists of non-cross-linked freeze-dried microfibrillated wood pulp cellulose. The last column in Table 1 indicates the percentage Z direction expansion, being 400% in the case of the product of Example 1.

The results in Table 1 indicate that at low density (0.04 g/cm$^3$), freeze-dried beaten non-cross-linked pulp MFCS-1 has about twice the absorption capacity and about quadruple the retention when compared to freeze-dried non-beaten non-cross-linked wood pulp control. However, after the material was densified by pressing to 0.4 g/cm$^3$ all the benefits obtained by fibrillation and freeze drying were lost. It will be noted that MFCS-IIa (product of Example 1), MFCS II (product of Example 1A) and MFCS-IIb (product of Example 2) achieve high absorbency at high density (0.4 g/cm$^3$). It is evident from the data in Table 1 that the densified, freeze-dried cross-linked microfibrillated cellulose pulp of the present invention is significantly superior in absorption and retention than its non-cross-linked counterpart MFCS-1 disclosed in U.S. Pat. No. 4,474,949. Cross-linking a non-fibrillated pulp fiber also improves the absorption capacity, but not to the extent that could be achieved by the microfibrillated batch. In this connection, it will be noted that the maximum capacity of MFCS-IIa at 0.40 g/cm$^3$ density is 20 g/g and the maximum capacity at 0.40 g/cm$^3$ density of MFCS-1 is only 6 g/g, i.e., over three times as great. It is thus very surprising that the process of the present invention provides such an extraordinary improvement over the process of U.S. Pat. No. 4,474,949.

While Table 1 indicates that a significant improvement was obtained with a density level of 0.4 g/cm$^3$, improvements have also been found to be quite evident at a density level of 0.1 g/cm$^3$ or higher.

In the process of present Example 1, as the water vapor in the frozen slurry is sublimed by the freeze-drying operation, the concentration of cross-linking chemicals increases drastically. The increase in zinc chloride concentration causes the fiber to swell, while at the same time enhancing the degree of cross-linking and yielding a product with both good absorbency and high wet resilience. The initial step in the swelling and dissolution of cellulose using zinc chloride was possibly due to the formation of an oxonium salt.

As may be seen from Table 1, different cross-linking agents are utilized; namely glutaraldehyde and zinc chloride combination, Polycup 2002 and a 37% W/V of formalin and zinc chloride combination. At a density of 0.4 g/cm$^3$, the product produced utilizing formalin as a cross-linking agent, possesses an absorption of 15 g/g and a retention of 9 g/g when tested by the porous plate method.

Normally, a 0.5M solution of cupriethylenediamine is a good solvent for cellulose, but if cross-linking is present, the latter solvent will not disolve the cross-linked product. Following the TAPPI method T-230 for viscosity measurements, it was observed that the MFCS-1 and virgin wood pulp easily dissolved in cupriethylenediamine but the product of present Example 1 (namely MFCS-IIa) did not dissolve therein. This phenomenon indicated the occurrence of cross-linking in the latter case.

The product of present Example 1 (namely MFCS-IIa) may be utilized to increase the total absorption capacity of napkins. The following tests set forth in Table 2 indicated that by inserting a 2.5 g MFCS-IIa board between the polyethylene barrier and the fluff portion of a commercial napkin known as Sure & Natural Maxishield, the total capacity of the latter product was increased by 37%.

TABLE 2

Effect of Insert on Total Absorption Capacity
For Sure & Natural Maxishields
Method: Fast Dynamic Form Test

| Insert Material* | Total Fluid Absorbed (cc) |
|---|---|
| Pulp Board | 56 |
| MFCS-IIa (Example 1) | 77 |

*2.5 grams of insert material were placed between the barrier and the fluff.

This increase is largely due to the fast wicking properties of MFCS-IIa (Table 3).

TABLE 3

Comparative Absorption Rate Data

| Materials | Density (g/cm$^3$) | 10 cm Wicking Time (Min.) | 7 cc Test (Min.) |
|---|---|---|---|
| Pulp Board | 0.55 | 9 | 17 |
| MFCS-IIa (Example 1) | 0.65 | 1 | 0.5 |

The fast wicking rate of the product of present Example 1 allows the fluid to be transported to all regions of napkins. The fast wicking is mainly due to densification of the MFCS-IIa. The densification reduces both the void volume and pore size. However, as soon as the fluid hits a certain spot the capillary size at that spot will increase. Hence the fluid front is moved rapidly through the large capillaries to the adjacent smaller capillaries.

The compressability of the MFCS-IIa in the dry state and its Z direction swelling in the wet state causes this material to be especially suitable for tampon applications. Samples of the densified product of present Example 1 prepared from a board and from chips were formed into compressed cylindrical tampons having a density of 0.45 and 0.43 g/cc respectively and these were compared with a commercial tampon known as o.b. Mini which is compressed to a density of 0.45 g/cm$^3$. (See the following Table 4). The o.b. Mini tampon comprises staple like fibers of rayon and cotton, and it is provided with a cover consisting of non-woven fusible fibers.

The capacity of the experimental and commercial tampons to absorb a one percent by weight aqueous sodium chloride solution under simulated in use conditions is determined by allowing one end of the tampon to be submerged in the liquid to be absorbed for a period of five minutes while maintaining the sides of the tampon under a confining pressure as set out in Table 4 below. The confining pressure is maintained by enveloping the tampon in a hydraulically inflated polyethylene sleeve. Excess fluid is drained from the tampon for a period of two minutes, the pressure is released, and the weight of the fluid absorbed by the tampon is determined and reported as Capacity, in units of weight of liquid absorbed per unit weight of the tampon.

TABLE 4

Material Testing for Tampon Application

| Material | N** | Density (g/cm$^3$) | Avg. Wt. (g) | Absorbency, $C_w$ (g/g) Pressure 24" | Pressure 8" |
|---|---|---|---|---|---|
| o.b. Mini (Tampon) | 10 | .45 | 2.2 | 3.2 | 4.9 |
| MFCS-IIa* (two 1.3 cm flat board) | 6 | .45 | 1.7 | 5.0 | 8.5 |
| MFCS-IIa* (2 × 2 mm chips) | 6 | .43 | 1.8 | 4.6 | 5.4 |

*Having an o.b. Mini cover.
**Number of samples.

From the above Table 4 it will be seen that the form of the MFCS-IIa has a pronounced effect on the final absorption properties. Tampons made from MFCS-IIa board had higher absorption properties than those made from MFCS-IIa chips. However, both construction prototypes resulted in higher absorption capacities than the o.b. Mini tampon.

From the above Tables 1 and 4 it will be noted that densified microfibrillated cross-linked cellulose (MFCS-IIa and MFCS-IIb) showed significantly higher fluid absorption and retention capacities than unbeaten or fibrillated non-cross-linked freeze-dried wood pulp. The fast wicking rate with Z direction swelling is attributed to chemical cross-linking of these fibers at low densities followed by their densification in the final dry state. Densification of the MFCS-IIa produces a flat, flexible board. Upon wetting, this board expands to a foam-like structure which has an enormous void volume available for liquid absorption.

While the invention has been described in terms of producing a highly absorbent cellulose pulp, nothing herein should be construed to suggest that the cellulose fibers cannot be otherwise additionally treated by other means to further enhance absorbency combined with other components to produce a composite material for absorbent purposes. Such modification, as well as others which will occur to one skilled in the art, are all within the scope of teachings of this invention.

We claim:

1. An absorbent product comprising, as an absorbent element therein, wet cross-linked and freeze dried microfibrillar pulp, said pulp comprising sheets of microfibrils arranged as discontinuous walls surrounding void volumes, said microfibrils having intermolecular cross-links between macromolecular chains, said absorbent element retaining good absorbency even after having been highly compressed to a sample density of at least 0.1 lg/cm$^3$.

2. The product of claim 1, said product having been densified under pressure to a sample density of at least about 0.4 g/cm$^3$.

3. The product of claim 2, wherein said pulp has a maximum Porous Plate Capacity of at least about 10 g/g with a testing fluid of 1% NaCl aqueous solution.

4. The product of claim 2, wherein said pulp has a Porous Plate Retention of at least about 5 g/g with a testing fluid of 1% NaCl aqueous solution.

5. The product of claim 3, wherein said pulp has a maximum Porous Plate Capacity of about 20 g/g.

6. The product of claim 4, wherein said pulp has a Porous Plate Retention of about 11 g/g.

7. The product of claim 2, said absorbent element demonstrating a uniaxial Z direction swelling in the wet state.

8. The product of claim 1, wherein said product is a sanitary napkin.

9. The product of claim 1, wherein said product is a catamenial tampon.

10. The product of claim 1, wherein said product is a disposable diaper.

11. The product of claim 1, wherein said product is a wound dressing.

12. The product of claim 1, wherein the starting cellulose fibers are wood pulp.

13. A process for preparing a highly absorbent retentive cellulose pulp, said pulp being capable of retaining good absorbency even after having been highly compressed to a sample density of at least about 0.1 g/cm$^3$, said process comprising:
  (a) forming a slurry, in a freeze drying medium, of cellulose fibers which have been beaten to a degree such that at least the outermost secondary walls thereof are essentially completely disintegrated into microfibrillar form, said freeze drying medium consisting of water or a non-aqueous solvent which is capable of hydrogen bonding with cellulose and which in pure form possesses a freezing point between 0° C. and 100° C., or a boiling point between 0° C. and 150° C. at normal pressure:
  (b) adding a cross-linking agent to said slurry and permitting cross-linking to commence; and
  (c) freeze drying said slurry;
whereby said highly absorbent, retentive, cross-linked cellulose pulp results.

14. The process of claim 13, which comprises additionally compressing said absorbent element to produce a densified thin sheet having a sample density of at least about 0.1 g/cm$^3$.

15. The process of claim 14, said absorbent element having been densified under pressure to a sample density of at least about 0.4 g/cm$^3$.

16. The process of claim 13, in which said cross-linking agent is selected from the group consisting of glutaraldehyde, a polyamine/amide epichlorohydrin adduct or formalin.

17. The process of claim 16, in which said cross-linking agent is a glutaraldehyde, catalyzed in zinc chloride.

18. The process of claim 16, in which said cross-linking agent is a polyamine/amide-epichlorohydrin adduct.

19. The process of claim 13, in which said non aqueous solvent is selected from the group consisting of t-butyl alcohol, benzene, hexafluorobenzene, 2-nitroisobutane, acetic acid, t-butyl mercaptan, cyclohexane, cyclohexyl fluoride, ethylene dibromide, 1,2 difluoro tetrachloroethane, glyoxal, and 2,2 dimethyl propionitrile.

20. The process of claim 17, in which said freeze drying medium is water.

21. The process of claim 18, in which said freeze drying medium is t-butyl alcohol.

22. An absorbent product, comprising, as an absorbent element therein, the cellulose pulp produced according to the process of claim 13.

23. An absorbent product, comprising, as an absorbent element therein, the cellulose pulp produced by the process of claim 14.

24. An absorbent product, comprising, as an absorbent element therein, the cellulose pulp produced according to the process of claim 15.

25. The product of claim 13, wherein said product is a sanitary napkin.

26. The product of claim 13, wherein said product is a catamenial tampon.

27. The product of claim 13, wherein said product is a disposable diaper.

28. The product of claim 13, wherein said product is a wound dressing.

29. The product of claim 13, wherein the starting cellulose fibers are wood pulp.

* * * * *

UNITED STATES PATENT AND TRADEMARK OFFICE
CERTIFICATE OF CORRECTION

PATENT NO. : 5,104,411

DATED : April 14, 1992

INVENTOR(S) : Kambiz B. Makoui et al.

It is certified that error appears in the above-identified patent and that said Letters Patent is hereby corrected as shown below:

Claim 1, column 14, line 4 "0.1 lg/cm$^3$." should be -- 0.1g/cm$^3$ --.

Signed and Sealed this

Ninth Day of November, 1993

*Attest:*

BRUCE LEHMAN

*Attesting Officer*   *Commissioner of Patents and Trademarks*